United States Patent
Bur et al.

(10) Patent No.: US 11,493,457 B2
(45) Date of Patent: Nov. 8, 2022

(54) METHOD AND DEVICE FOR THE X-RAY INSPECTION OF PRODUCTS, IN PARTICULAR FOODSTUFFS

(71) Applicant: Wipotec GmbH, Kaiserslautern (DE)

(72) Inventors: Christian Bur, Saarbrücken (DE); Marco Wickert, Kaiserslautern (DE)

(73) Assignee: Wipotec GmbH, Kaiserslautern (DE)

(*) Notice: Subject to any disclaimer, the term of this patent is extended or adjusted under 35 U.S.C. 154(b) by 57 days.

(21) Appl. No.: 16/858,974

(22) Filed: Apr. 27, 2020

(65) Prior Publication Data
US 2020/0348247 A1    Nov. 5, 2020

(30) Foreign Application Priority Data

May 3, 2019 (DE) .......................... 102019111567.1

(51) Int. Cl.
*G01N 23/04* (2018.01)
*G01N 23/083* (2018.01)
(Continued)

(52) U.S. Cl.
CPC ........... *G01N 23/04* (2013.01); *G01N 23/083* (2013.01); *G01N 23/087* (2013.01); *G01N 23/18* (2013.01);
(Continued)

(58) Field of Classification Search
CPC .... G01N 23/04; G01N 23/083; G01N 23/087; G01N 23/18; G01N 2223/1016;
(Continued)

(56) References Cited

U.S. PATENT DOCUMENTS

| 4,651,005 A | * | 3/1987 | Baba | G01T 1/247 |
| | | | | 250/370.06 |
| 4,794,257 A | * | 12/1988 | Baba | A61B 6/4441 |
| | | | | 250/370.01 |

(Continued)

FOREIGN PATENT DOCUMENTS

| EP | 2405260 A1 | 1/2012 |
| EP | 2588892 B1 | 5/2013 |

(Continued)

OTHER PUBLICATIONS

Japan Patent Office Action dated May 21, 2021 in Japan patent application No. 2020-077279.

(Continued)

*Primary Examiner* — Allen C. Ho
(74) *Attorney, Agent, or Firm* — The Culbertson Group, P.C.

(57) ABSTRACT

A method for the X-ray inspection of products of a predefined product type including at least one first component and one second component having different absorption coefficients for X-radiation. X-radiation with a spectral range is transmitted through a product to be examined. The X-radiation that has passed through the product is detected by means of a spectrally resolving X-ray detector. The spectrally resolving X-ray detector assigns the X-ray quanta to a number of energy channels and generates image data which for each pixel include spectral values for selected or all energy channels and/or total spectral values for one or more groups of adjacent energy channels. At least one mapping rule is used to process the image data to form a total image, where each mapping rule is designed such that spectral values or total spectral values are mapped onto a total image value of an image point.

16 Claims, 5 Drawing Sheets

(51) Int. Cl.
*G01N 23/087* (2018.01)
*G01N 23/18* (2018.01)

(52) U.S. Cl.
CPC .............. *G01N 2223/1016* (2013.01); *G01N 2223/618* (2013.01)

(58) Field of Classification Search
CPC ....... G01N 2223/618; G01N 2223/501; G01N 2223/5015; G01N 2223/2013
USPC .......... 378/53, 54, 57, 58, 98.9, 98.11, 98.8
See application file for complete search history.

(56) References Cited

U.S. PATENT DOCUMENTS

| | | | | |
|---|---|---|---|---|
| 5,247,559 | A * | 9/1993 | Ohtsuchi | A61B 6/482 378/53 |
| 5,917,877 | A * | 6/1999 | Chiabrera | A61B 6/583 378/207 |
| 5,943,388 | A * | 8/1999 | Tümer | G01V 5/0041 378/98.9 |
| 6,018,562 | A * | 1/2000 | Willson | G01N 23/087 378/57 |
| 6,122,344 | A * | 9/2000 | Beevor | G01V 5/0025 378/57 |
| 6,173,038 | B1 * | 1/2001 | Siffert | A61B 6/482 378/174 |
| 6,246,747 | B1 * | 6/2001 | Wear | G01T 1/29 378/98.9 |
| 6,248,990 | B1 * | 6/2001 | Pyyhtiä | G01T 1/247 250/370.08 |
| 6,255,654 | B1 * | 7/2001 | Verbinski | G01N 23/02 378/57 |
| 6,335,960 | B2 * | 1/2002 | Knigge | G01N 23/02 378/57 |
| 6,408,050 | B1 * | 6/2002 | Han | G01T 1/2928 378/98.9 |
| 6,449,334 | B1 * | 9/2002 | Mazess | G01N 23/083 378/53 |
| 6,570,955 | B1 | 5/2003 | Siffert | |
| 6,574,303 | B2 * | 6/2003 | Sawada | G01N 23/04 378/58 |
| 6,661,868 | B2 * | 12/2003 | Sawada | G01N 23/04 378/57 |
| 7,099,433 | B2 * | 8/2006 | Sommer | G01N 23/083 378/53 |
| 7,123,685 | B2 * | 10/2006 | Ostergaard | G01N 33/12 378/53 |
| 7,369,642 | B2 * | 5/2008 | Eilbert | G01V 5/0016 378/57 |
| 7,634,061 | B1 * | 12/2009 | Tümer | G01T 1/249 378/62 |
| 7,983,387 | B1 * | 7/2011 | Toh | G01N 23/203 378/57 |
| 8,000,440 | B2 * | 8/2011 | Petch | G01V 5/0016 378/53 |
| 8,223,922 | B2 * | 7/2012 | Suyama | G01N 23/087 378/98.9 |
| 8,280,005 | B2 * | 10/2012 | Suyama | G01N 23/04 378/98.9 |
| 9,014,455 | B2 * | 4/2015 | Oh | A61B 6/405 382/132 |
| 9,031,197 | B2 * | 5/2015 | Spahn | G01T 1/172 378/98.8 |
| 9,274,235 | B2 * | 3/2016 | Kang | A61B 6/4241 |
| 9,448,310 | B2 * | 9/2016 | Han | G01T 1/2914 |
| 9,464,996 | B2 * | 10/2016 | Marche | G01N 23/083 |
| 9,517,045 | B2 * | 12/2016 | Kang | A61B 6/4233 |
| 9,706,967 | B2 * | 7/2017 | Wang | A61B 6/4241 |
| 9,791,384 | B2 * | 10/2017 | Sung | G01N 23/04 |
| 9,867,580 | B2 * | 1/2018 | Danielsson | A61B 6/03 |
| 9,885,674 | B2 | 2/2018 | Ouvrier-Buffet | |
| 10,061,038 | B2 * | 8/2018 | Cao | G01T 1/244 |
| 10,083,520 | B2 * | 9/2018 | Kim | G06V 10/10 |
| 10,261,033 | B2 * | 4/2019 | Jimenez, Jr | G01V 5/00 |
| 10,416,342 | B2 * | 9/2019 | Scoullar | G01V 5/0041 |
| 10,502,698 | B2 * | 12/2019 | Yamakawa | G01N 23/18 |
| 10,677,942 | B2 * | 6/2020 | Cao | G01T 1/247 |
| 10,697,904 | B2 * | 6/2020 | Yamakawa | G01T 1/2928 |
| 10,698,122 | B2 * | 6/2020 | Iwashita | A61B 6/4241 |
| 10,718,725 | B2 * | 7/2020 | Miyazaki | G06T 7/0008 |
| 10,724,969 | B2 * | 7/2020 | Xing | A61B 6/5205 |
| 10,816,485 | B2 * | 10/2020 | Jimenez, Jr. | G01V 5/00 |
| 10,852,257 | B2 * | 12/2020 | Powell | G01N 23/10 |
| 10,948,613 | B2 * | 3/2021 | Cao | A61B 6/4233 |
| 10,969,220 | B2 * | 4/2021 | Brambilla | G01N 23/087 |
| 10,983,070 | B2 * | 4/2021 | Paulus | G01N 23/04 |
| 11,009,470 | B2 * | 5/2021 | Yamakawa | G01N 23/083 |
| 11,016,040 | B2 * | 5/2021 | Yamakawa | A61B 6/502 |
| 11,073,486 | B2 * | 7/2021 | Siegrist | G01N 23/083 |
| 11,099,141 | B2 * | 8/2021 | Yamakawa | G01N 23/04 |
| 11,112,528 | B2 * | 9/2021 | Xu | G01N 23/087 |
| 11,150,203 | B2 * | 10/2021 | Zhu | G01N 33/2823 |
| 11,243,327 | B2 * | 2/2022 | Scoullar | G01V 5/0041 |
| 11,331,068 | B2 * | 5/2022 | Yamakawa | G01N 23/087 |
| 2012/0213331 | A1 | 8/2012 | Peschmann | |
| 2018/0214113 | A1 | 8/2018 | Yamakawa | |
| 2018/0336672 | A1 | 11/2018 | Perticone | |

FOREIGN PATENT DOCUMENTS

| | | |
|---|---|---|
| JP | 2869975 B2 | 3/1999 |
| JP | 2018155754 A | 10/2018 |
| WO | 2017069286 A1 | 4/2017 |
| WO | 2017205914 A1 | 12/2017 |
| WO | 2018102051 A1 | 6/2018 |
| WO | 2018217738 A1 | 11/2018 |

OTHER PUBLICATIONS

European Patent Office extended search report dated Oct. 30, 2020 in European patent application No. 20 17 2056.2.

* cited by examiner

|  | Channel1 | Channel2 | Channel3 | ... | Channel256 | Class Y |
|---|---|---|---|---|---|---|
| Image "product" 1 | | | | | | product |
| Image "product" 2 | | | | | | product |
| Image "product" 3 | | | | | | product |
| ... | | | | | | product |
| Image "product" P | | | | | | product |
| Image "contamination" 1 | | | | | | contamination |
| Image "contamination" 2 | | | | | | contamination |
| Image "contamination" 3 | | | | | | contamination |
| ... | | | | | | contamination |
| Image "contamination" C | | | | | | contamination |

Fig. 8

METHOD AND DEVICE FOR THE X-RAY INSPECTION OF PRODUCTS, IN PARTICULAR FOODSTUFFS

TECHNICAL FIELD OF THE INVENTION

The invention relates to methods and devices for inspecting products, in particular foodstuffs, using X-radiation.

BACKGROUND OF THE INVENTION

Line detectors, which are provided transverse to the movement direction of the products to be examined, are usually used for the X-ray inspection of moving products. Instead of the product moving, the entire X-ray inspection device or at least the relevant X-ray detector device can also be moved relative to the product to be examined. The product to be examined is scanned by means of the line detector, which detects the X-radiation generated by one or more X-ray sources, and the image data generated line by line are converted to an image of the product to be examined. To generate the image, the image data can be processed in a suitable manner. The thus-generated image can be inspected by image processing. In particular, the image of the product to be examined can be inspected for whether one or more predefined product features are present or achieved. For example, a foodstuff, for example a piece of meat, can be examined for whether there are undesired foreign bodies in it, such as bone fragments, metal swarf from processing machines, glass splinters, plastics, stones or the like.

For this purpose, it is known to use spectrally integrating line detectors (non-spectral detectors) which detect virtually the entire width of the X-ray spectrum of the X-radiation which is generated by the relevant X-ray source. Such line detectors have a comparatively high spatial resolution in the region of for example 0.2 mm over a total detector width of from, for example, 200 to 800 mm or more. The line detectors can be constructed in the form of modules, which can be coupled together with in each case only very small gaps of only a few pixels (for example one to two pixels per module edge) until a desired scan width is achieved. Even very small foreign bodies or contaminations are thus detectable with such non-spectral detectors. This type of detector moreover requires no cooling and is cost-effective to produce.

However, as a result of the spectral integration such non-spectral detectors generate only grayscale values. A grayscale value is dependent on the attenuation of the X-radiation when it passes through the product to be examined. The attenuation is in turn dependent on the thickness of the product and on the material properties.

This type of sensor is suitable in particular for detecting extremely small, strongly absorbing foreign bodies, for example metal splinters.

An improvement in the contrast of the image generated by line detectors can be achieved through the dual energy method. There, two line detectors are used, the scan images of which are superimposed. The line detectors capture different spectral ranges of the X-radiation that has passed through the product. This is achieved through the use of at least one X-ray filter, which is arranged in front of one of the non-spectral detectors in the beam path. However, such filters operate only as high-pass filters and moreover cannot be produced sufficiently flexibly with respect to the desired filter edge. In addition, they also attenuate the X-radiation to be detected in the desired spectral range. Through the separate capture of different spectral ranges a different item of information is contained in the image signals of the respective line detectors. A total image which has a better contrast than a single-energy image with respect to the recognizability of particular foreign body materials can be generated through a weighted superimposition (for example correctly signed addition of the weighted image data). With a fixed X-ray filter, however, the contrast can only be improved for one or more particular materials. Dual energy methods are therefore not very flexible with respect to their use, as the X-ray filter must be chosen suitably, depending on the application case.

Moreover, the spectral ranges of the X-radiation which are captured by the two line detectors usually overlap, with the result that a portion of the same item of information is contained in each of the two image signals. An optimum contrast improvement thus cannot be achieved.

However, the dual energy method makes it possible to remove product regions of a product consisting of only two materials when the two image signals are combined suitably. Thus, for example, the contrast in the region of a foreign body, i.e. of a first material, inside the product, i.e. a second material, can be optimized. However, this only applies to a substantially homogeneous product made of a single material (or a combination of materials with very similar attenuation properties for the X-radiation), in which foreign bodies made of a further material (with different attenuation properties for the X-radiation) are contained.

Furthermore, in recent years spectrally resolving line detectors have been developed which can likewise be coupled modularly. However, such spectral line detectors, which make sufficiently large scan widths of from 200 to 800 mm or more possible, are currently only available with a relatively coarse spatial resolution, i.e. with a relatively large pixel pitch, of for example 0.8 mm. Such spectral line detectors are capable of capturing the entire spectral width of the X-radiation to be detected, for example in the range of from 20 keV to 160 keV. These detectors provide a large number of energy channels, for example up to 256, for the spectral resolution. Such a spectral line detector therefore makes it possible to generate a number of partial images corresponding to the number of energy channels.

To date, such line detectors have in practice mostly been used to recognize particular materials (e.g. EP 2 588 892 B1), wherein for this purpose the energy spectrum ascertained for a product is standardized by means of the energy spectrum of a light image, i.e. the spectrum which is ascertained by the detector without the presence of a product. The natural logarithm of the spectrum standardized in this way corresponds to the product of the energy-dependent absorption coefficient for the product multiplied by the thickness of the product. The spectral progression of the energy-dependent absorption coefficient thus ascertained for an unknown product can be compared with the known product data. In this way it is possible to identify the material of an unknown product.

In the food industry, there is often the problem of recognizing product contaminations, i.e. undesired foreign bodies in a desired product. If the products to be examined have variations in the thickness, known methods do not provide reliable information as to whether variations in the grayscale value in an image which is generated by one or more non-spectrally resolving detectors are generated by variations in the thickness of the product to be examined without the presence of a foreign body to be detected or by the material of a foreign body which has a deviating absorption for the X-radiation.

Moreover, known methods and devices for the X-ray inspection of products often provide only grayscale images (this also applies to dual energy methods) which do not have a sufficient contrast for a reliable evaluation.

SUMMARY OF THE INVENTION

An object of the invention is to provide a method for the X-ray inspection of products, in particular foodstuffs, which improves the recognition of foreign bodies in a product, and/or to provide at least an estimate of the thickness of a product including two or more components or of the total thickness of one or more components of a product. A further object of the invention is to provide a device for carrying out the method.

The various aspects of the present invention employ a spectrally resolving X-ray detector to recognize foreign bodies in a product. Moreover, information on the thickness of products can be obtained from the detected data if the nature of the product, for example of a foodstuff, such as meat with a meat content and a fat content, is known.

In a method according to one aspect of the invention, at least one product type is defined, which comprises products which include at least one first and one second component, which have different absorption coefficients for the X-radiation. In the case of applications in the food industry, they can be pieces of meat which have the components meat, fat and bone. In this case, it is usually desirable to ascertain the presence of bone and the size and position thereof. Moreover, there is often a desire to at least estimate the meat content and the fat content. In the food industry, the product type can, however, also be any other products which are to be examined with respect to similar properties. For example, yogurt can be examined for the presence of foreign bodies, such as steel wear debris or plastic particles. Of course, not only packaged goods, but also any kind of product, even bulk goods such as cereal, flour or the like, can be examined in a corresponding manner.

Methods according to this first aspect of the invention include transmitting X-radiation with a predefined spectral width (that is, range) through the product to be examined, which belongs to the at least one product type, and detecting the X-radiation that has passed through the product where the detection is accomplished by means of a spectrally resolving X-ray detector. The X-ray detector has a predefined number of pixels, at which the X-radiation is detected spectrally resolved. The X-ray quanta for the spectral resolution are assigned, depending on their energy, to a predefined number of energy channels. In this way, the X-ray detector generates image data which, for each pixel, include spectral values for selected or all energy channels and/or total spectral values for one or more groups of adjacent energy channels.

To process the image data to form a total image, at least one mapping rule is determined for the at least one product type, wherein each mapping rule is designed such that all spectral values and total spectral values are mapped onto a total image value of an image point of the total image, wherein one mapping rule is assigned in each case to all pixels or predetermined groups of one or more pixels. The variant according to which a mapping rule is assigned not to all pixels, but only to a group of pixels is of interest whenever the X-ray detector has different sensitivities. Usually, such a spectrally resolving X-ray detector has crystals which serve to detect the X-ray quanta. These crystals usually cannot be manufactured with a geometric extent which corresponds to the desired detector surface area or detector length, with the result that when several such crystals are combined to form one X-ray detector different sensitivities of the crystals have to be compensated for.

At this point it may be pointed out that the X-ray detector can be designed as a line detector or as a flat panel detector. As it is often necessary in the food industry to examine moving products over a width of up to 800 mm or more, line detectors are usually used, because flat panel detectors having such a width would be too expensive.

According to one embodiment of a method according to the invention, the one or more mapping rules are determined such that, in the total image of a product of the at least one product type, one or more components undergo an increase in contrast relative to a reference component, in comparison with a grayscale image which would be generated by the simple addition of all or selected spectral values and all or selected total spectral values to form total image points. In other words, the spectral evaluation using a suitable mapping rule causes the given component to undergo an enhancement in contrast relative to another component and thus makes it possible to improve the recognizability of product regions with in each case different material properties compared with the use of non-spectrally resolving X-ray detectors, which generate only a simple grayscale image.

According to another embodiment of a method according to the invention, the one or more mapping rules are chosen such that the total image value of an image point represents either a value for the total thickness of the first component or a value for the total thickness of the second component, viewed in the irradiation direction. This embodiment of the invention can advantageously be used in particular for product types the products of which consist of precisely two components.

In this thickness imaging embodiment, at least one first mapping rule is preferably used, which provides information on the total thickness of the meat portion during the examination of a product of a known product type, for example a piece of meat with a fat content. By total thickness is meant here the sum of all layer thicknesses which, viewed in the irradiation direction, consist exclusively or substantially of meat. In addition, at least one second mapping rule is used, which provides information on the total thickness of the fat portion. None of the at least one first or second mapping rules is capable of providing an item of information on the overall thickness of the product. However, this can be ascertained for the respective total thickness of the individual components by the addition of the values determined by the in each case at least one first and the in each case at least one second mapping rule.

According to a further embodiment within the scope of the present invention, the at least one mapping rule represents a classifier, which assigns the at least two components to predefined classes. Each class is identified by a numerical target value. For example, in a piece of meat which includes meat and bone, the bone can be considered to be undesired (and equated to an undesired foreign body) and the meat portion can be considered to be desired.

The classifier can be in particular an artificial neural network or a support vector machine.

According to a further embodiment, the at least one mapping rule can be determined such that a mapping coefficient is assigned to each spectral value or each total spectral value, and that the total image of the product to be examined is generated by multiplying each spectral value and each total spectral value by the assigned mapping coefficient and adding these products together. While the above-described classifier embodiments require a supervised learning of the classifier, this latter embodiment also makes a non-supervised learning possible.

In addition, this latter embodiment makes the advantageous generation of a dual energy image possible if this linear mapping rule is determined such that a dual energy image or multiple energy image is generated from the image data by multiplying the spectral values from at least two groups of selected adjacent energy channels or corresponding total spectral values by in each case a constant weighting factor and adding these products together.

The spectrally resolving X-ray detector provides the possibility of freely choosing the spectral ranges which are used to generate the dual energy image. Both the width of the spectral ranges and the position thereof can be chosen as desired. Moreover, a single set of image data (i.e. the image of a product to be examined) can also be evaluated several times with a single detection operation, in particular using different mapping rules, i.e. different spectral ranges which are combined to form a dual energy image. Total images can thus be generated, which are optimized with respect to the recognition of particular materials, in particular foreign bodies made of particular materials (for example steel, plastic, bone or the like).

According to a further embodiment, the at least one mapping rule can be determined such that the groups of adjacent energy channels do not overlap spectrally, or that the X-ray detector is operated or actuated such that the image signal only includes spectral values for non-overlapping groups of energy channels or already includes total spectral values for non-overlapping groups of energy channels. A dual energy image can thus be generated, which is generated by combining completely disjoint spectral ranges. Compared with dual energy images which are generated with conventional, non-spectrally resolving X-ray detectors, an improved contrast can hereby be produced between image regions which correspond to product regions which have different material combinations in the irradiation direction.

According to an additional embodiment of the invention, the at least one mapping rule can be determined by means of a machine learning process, wherein, in a learning mode, a multiplicity of training products, which include in each case of one of the components and have different thicknesses, are detected by means of the spectrally resolving X-ray detector, and wherein, in order to determine each mapping rule, the spectral values or total spectral values of all or selected pixels or groups of adjacent pixels which are detected for the training products are used as features of the mapping rule, and predefined class values are used as target values of the mapping rule, wherein the class value for all training products which include the same component is identical. The detected spectral values or total spectral values in these embodiments may be for all or selected pixels of the X-ray detector or groups of adjacent pixels.

Implementations according this additional embodiment determine the properties of the at least one mapping rule in such a way that a total image is generated, which arises through classification and can consequently be regarded as a score image.

According to a further embodiment, simulation data can be used instead of detected spectral values or total spectral values which are obtained for a training product including a component with a known material, wherein the simulation data comprise products of previously known values for the energy-dependent mass attenuation coefficient (absorption coefficient is equal to the mass attenuation coefficient times the density of the material) and suitably chosen thicknesses.

This procedure using simulation data is suitable in particular when the intention is to recognize foreign bodies which consist of a known material, for example steel or particular plastics, in a product and when data for the energy-dependent absorption coefficient are already available for this material, which are either stored in the inspection device itself or in an external database. In this variant, the absorption coefficient must therefore be determined for the relevant material at the locations (or in the respective regions) of the energy channels of the X-ray detector. The relevant values must be multiplied in each case by an assumed thickness of the material. Such a value corresponds to the value which the X-ray detector would detect during the irradiation of such a material, based on the respective light image.

For the thickness of the training products and also for the thickness for generating the simulation data, values are preferably used which cover the range which is to be expected in practice during the check of the products of the relevant product type.

According to another embodiment of the invention, the at least one mapping rule for the at least one product type for determining the total thickness of the first or the second component is likewise determined by means of a machine learning process, wherein, in a corresponding learning mode, at least one first mapping rule for determining the total thickness of the first component and at least one second mapping rule for determining the thickness of the second component are ascertained, and wherein, in the learning mode, a multiplicity of training products which include both components are detected by means of the spectrally resolving X-ray detector. Training products which have an in each case different previously known total thickness of the first component and an identical or different total thickness of the second component are used to determine the at least one first mapping rule, and training products which have an in each case different previously known total thickness of the second component and an identical or different total thickness of the first component are used to determine the at least one second mapping rule. Alternatively, training products which have an in each case different previously known total thickness of the first component and an identical or different previously known total thickness of the second component can be used to determine the at least one first and second mapping rules. In order to determine the at least one first and second mapping rules, the spectral values or total spectral values which are detected for the training products are used as features of the mapping rule and in each case previously known total thicknesses are used as target value of the mapping rule. Such spectral values or total spectral values may be for all or selected pixels or for groups of adjacent pixels.

According to an embodiment of the invention, several product types can be defined, wherein each product type comprises products which include in each case the same first and at least one second component, which have different absorption coefficients for the X-radiation. Thus, several total images can be generated using the same image data of a product to be examined, wherein one mapping rule for an in each case different product type is used to generate each total image.

These and other advantages and features of the invention will be apparent from the following description of representative embodiments, considered along with the accompanying drawings.

BRIEF DESCRIPTION OF THE DRAWINGS

FIG. 8 is a table to illustrate evaluation methods for the image data.

DESCRIPTION OF REPRESENTATIVE EMBODIMENTS

Figure 1:
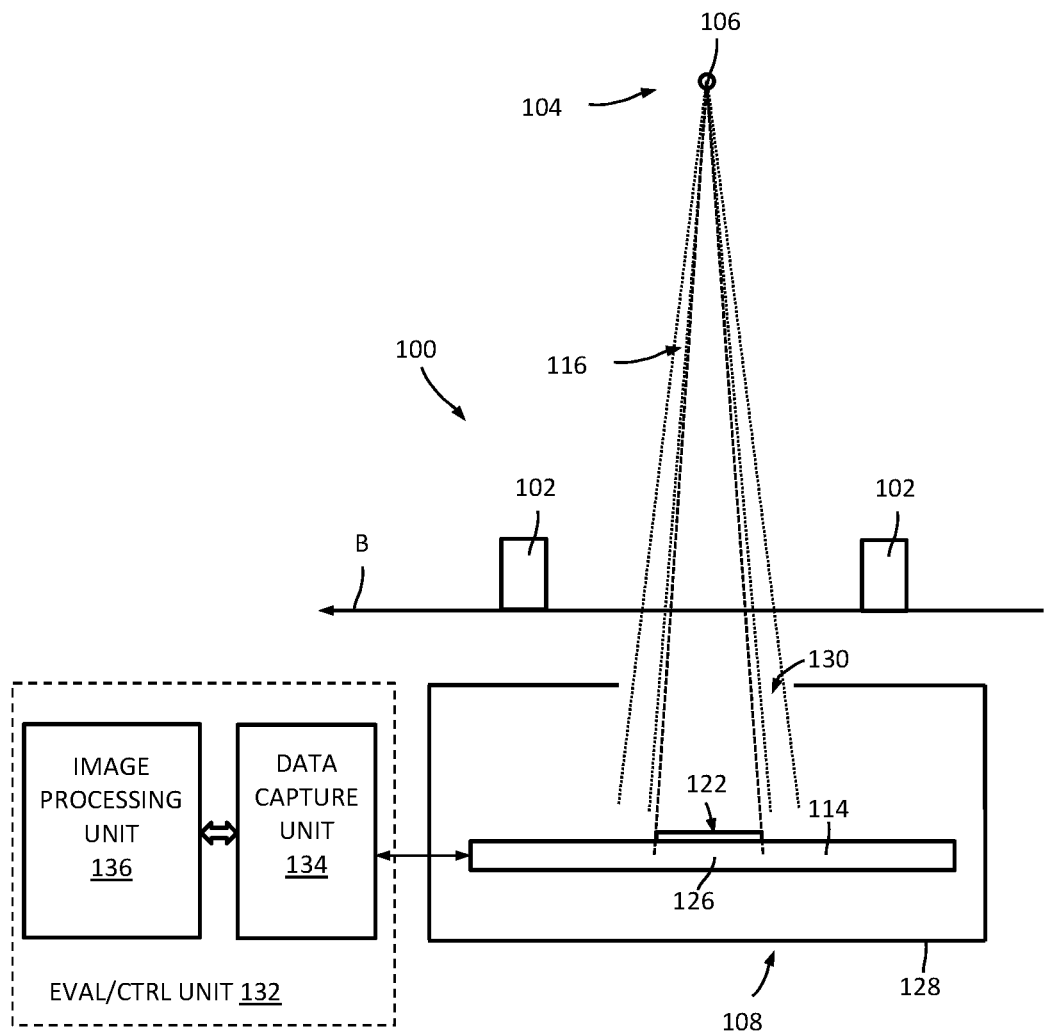
FIG. 1 is a schematic representation of an embodiment of a device for the inspection of products with a spectrally resolving line detector.

FIG. 1 shows a schematic representation of a first embodiment of a device 100 for the X-ray inspection of products 102, in particular foodstuffs, with a radiation-generating device 104 with at least one X-ray source 106 with an X-ray detector device 108 and with a spectrally resolving X-ray detector 1H, which is designed as a line detector 114.

The X-ray source 106 generates a fan-shaped X-ray beam 116, which has a center plane which is perpendicular to a movement direction B, in which the products 102 to be examined are moved through the X-ray beam 116. In a plane along the movement direction B, the X-ray beam 116 has an angle which is designed such that the X-ray beam 116 is transmitted through the product 102 to be examined in its entire width. A conveying device (not represented), for example a conveyor belt, can be provided to move the product 102.

The line detector 114 comprises a detector line 122 which can have a discrete spatial resolution, i.e. a pixel pitch, of for example 0.8 mm. The detector line 122 is provided approximately in the middle on a carrier 126, which can also carry heat sinks and other components. The heat sinks can also form the carrier 126.

The line detector 114 can, as shown in FIG. 1, be provided in a housing 128, which can be designed as a radiation protection housing. On its upper side, i.e. the side facing the X-ray source 106, the housing 128 has an opening 130 which makes it possible for the X-ray beam 116 to penetrate into the housing 128 in the direction of the detector line 122 of the line detector 114.

Two or more spectrally resolving line detectors can also be provided instead of a single spectrally resolving line detector 114. This can be advantageous when the spectrally resolving line detectors are designed in each case to capture a different maximum spectral width. For example, one of the spectrally resolving line detectors can have a spectral width of from at most 20 keV to 160 keV with a spectral resolution of 256 energy channels and a further spectrally resolving line detector can have a spectral width of from at most 20 keV to 80 keV, likewise with a resolution of 256 energy channels. The further spectrally resolving line detector thus has a spectral resolution that is twice as high as that of the first spectrally resolving line detector.

The line detector 114 generates an image data signal, which is fed to an evaluation and control unit 132. The evaluation and control unit 132 can have a data capture unit 134 and an image processing unit 136. The image data signal of the line detector 114 is fed to the data capture unit 134. The image processing unit 136 is designed for the further processing and analysis of the image data. The data capture unit 134 can also be designed such that it actuates the line detector 114 suitably, in particular with respect to the scanning time points. For this purpose, the data capture unit 134 can feed a clock signal to the line detector, wherein the image data capture by the line detector can be effected synchronized with the clock signal.

The image processing unit 136 can process the image data captured by the line detector 114 in the following manner.

Figure 2:
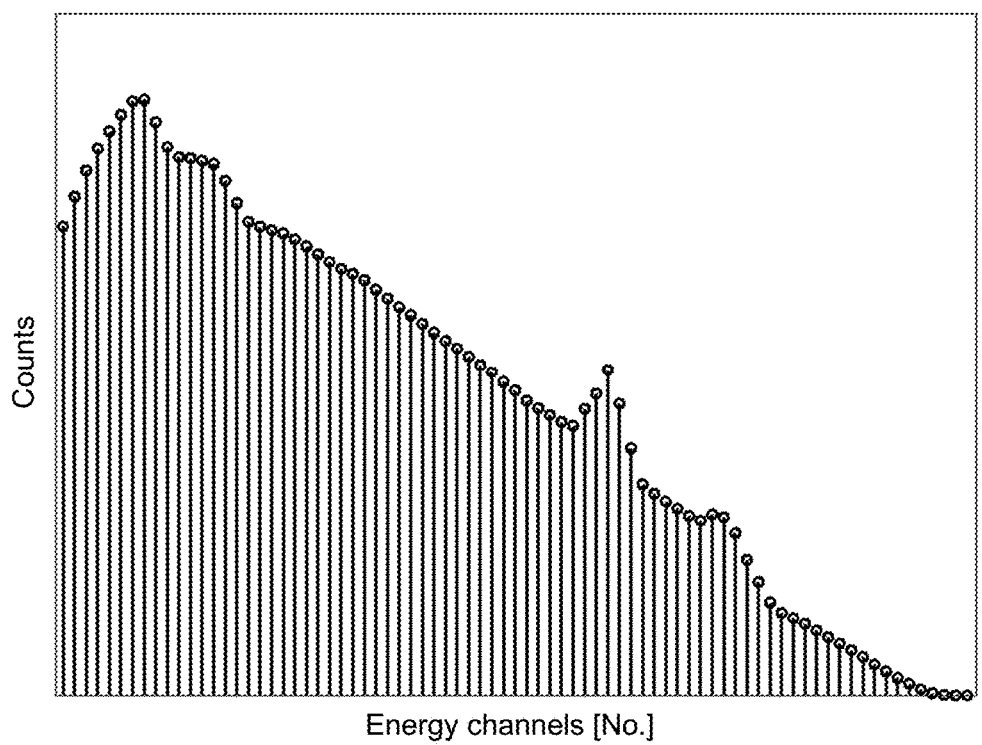
FIG. 2 is an example of an energy spectrum which was generated by a pixel of a spectrally resolving line detector.

FIG. 2 shows by way of example the image data which are provided by the spectrally resolving line detector 114 for a particular pixel. Here, the entire captured energy range, for example from 20 keV to 80 keV, is divided into a particular number of energy channels, wherein each energy channel has a particular (usually constant) spectral width, which results from the width of the entire captured spectral range divided by the number of energy channels, for example 128 or 256 energy channels. The line detector 114 provides one spectral value, which is denoted by "counts" in FIG. 2 because such a spectrally resolving line detector as a rule counts individual photons, for each energy channel and assigns the recorded photons, depending on their energy, to a particular energy channel. The progression represented in FIG. 2 corresponds to a typical light image which is generated by the line detector 114 without the presence of a product in the beam path of the X-ray beam 116. This spectrum is altered characteristically if a product made of a particular material or a particular material combination lies in the beam path of the X-radiation which is detected by the pixel.

The spectral values are transmitted with the image data signal to the evaluation and control unit 136 as image data. The evaluation and control unit 136 can evaluate these image data in different ways.

For example, the capacity of a spectral resolution of the line detector 114 can be utilized in order to generate a dual energy image. For this purpose, the evaluation and control unit 136 can perform any desired weighting of the spectral values pixel by pixel. Such a weighting can be effected in that a factor, which is multiplied by the respective spectral value, is assigned to each individual energy channel. A severe restriction of the spectrum can also be achieved hereby, if the factor zero is assigned to selected energy channels.

Figure 3:
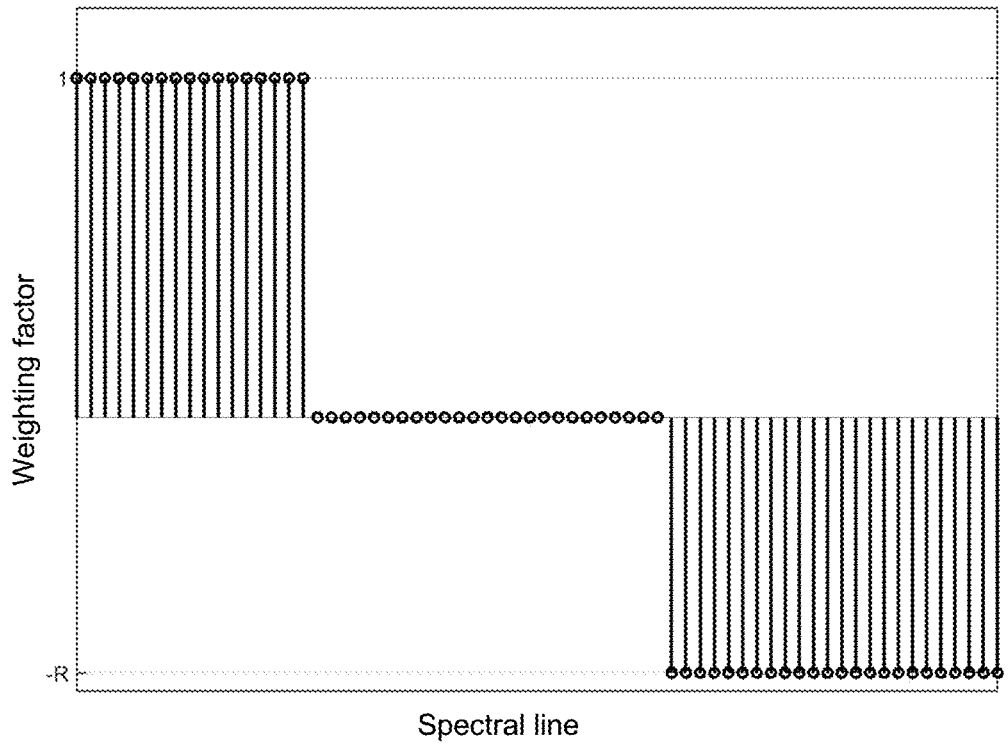
FIG. 3 is a weighting profile for weighting the energy channels of an energy spectrum according to FIG. 2 for generating a dual energy image.
Figure 4:
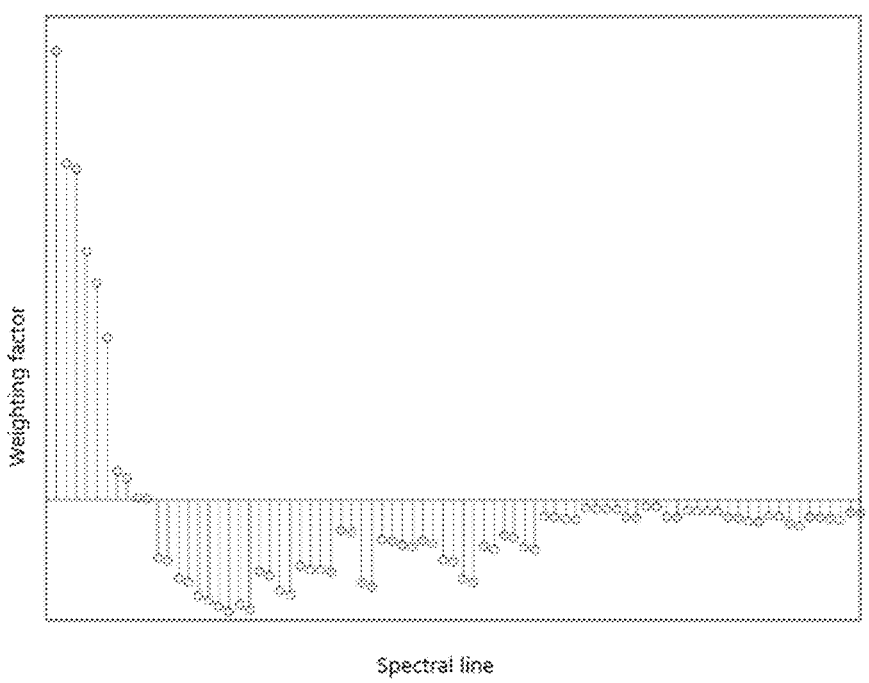
FIG. 4 is a weighting profile for weighting the energy channels of an energy spectrum according to FIG. 2 for generating a score image.
Figure 7:
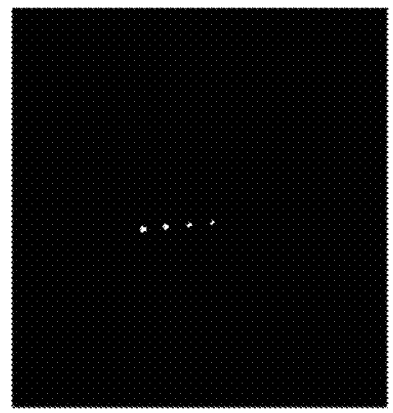
FIG. 7 is a second score image which is optimized for the visualization of the foreign bodies made of the second material.

FIG. 3 shows a weighting profile which has a separate weighting factor for each energy channel. This profile provides in each case a constant weighting for a number of energy channels in the lower range of the entire spectrum and in the upper range of the spectrum, for example with a factor 1 in the lower spectral range and with a factor −R in the upper spectral range. All other energy channels are weighted with the factor 0. The thus-weighted spectral values of the energy channels can be added together to generate a total spectral value, resulting in a dual energy image.

As already explained above, the spectrally resolving line detector 114 can also be designed such that it preselects which energy channels are transmitted to the evaluation and control unit 136 as part of an image data signal. For example, the line detector 114 can be adjusted manually or by the evaluation and control unit 136 such that it emits only particular energy channels as an image data signal. The line detector 114 can also be designed such that it emits the selected energy channels already integrated, i.e. it adds up the spectral values of the selected energy channels. In this case, a less complex processing of the image data of the line detector 114 results for the evaluation and control unit 136.

The spectrally resolving line detector 114 thus makes it possible to generate a dual energy image using a flexible spectrum. This can be established through the simple evaluation of the image data signal of the line detector 114, or the line detector 114 is actuated such that it already provides corresponding spectrally restricted image data or even total spectral values (see above).

The spectrum of the spectrally resolving line detector 114 can be varied such that particular product features of a product to be examined can be better recognized in the dual energy image, for example with a higher contrast.

The evaluation of the image data obtained by means of a single scan can also be effected such that several evaluations are carried out. In particular, different dual energy images can be generated using differently weighted image data of the spectrally resolving line detector 114. For example, the spectrum of the image data of the line detector 114 in an evaluation can be chosen (for example through a corresponding weighting) such that foreign bodies made of a particular material, for example steel, can be recognized with high contrast. In a further evaluation, the spectrum of the image data of the line detector 114 can be chosen differently, for example in order to generate a dual energy image in which foreign bodies made of a different material, for example polyethylene, are to be recognized with high contrast.

How the complete information which is contained in the spectral image data can be used by an advantageous image evaluation is explained in the following.

For this purpose, a training phase is run through first, for which the evaluation and control unit can be converted to a training mode. In the training phase at least one mapping rule is determined, which maps all or selected spectral values and total spectral values onto a total image value of an image point of the total image, or which maps all or selected spectral values and total spectral values onto a total image value of an image point of the total image, which represents a value for the total thickness of a component of the irradiated product, viewed in the irradiation direction.

Figure 6:
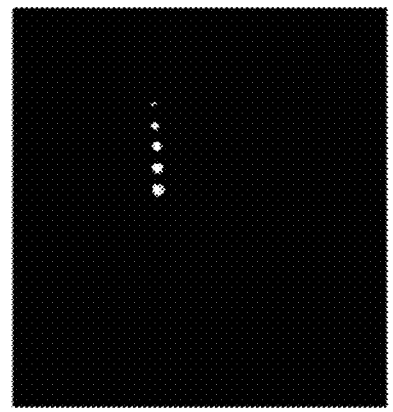
FIG. 6 is a first score image which is optimized for the visualization of the foreign bodies made of the first material.

For example, in the training phase the individual pixels of the recorded product images with their associated 256 energy channels can be arranged in the form of a table, as represented in FIG. 6. Here the pixels form the rows; so-called observations. The energy channels of each pixel form the columns and are referred to as features.

A class value Y (target value) is assigned to each row of the table, and thus to each pixel. This can be—depending on the application—either a discrete class name or a class identification number in the case of a contrast optimization, or a layer thickness value in the case of a layer thickness determination, for example the layer thickness in mm. Thus, in the training phase the features and the class values are known and it is necessary to determine a mapping rule.

In the case of a contrast optimization for products to be examined which might have a contamination with foreign bodies, several images of a first component (uncontaminated product), preferably with different thicknesses, can be recorded for the training process. A class value, e.g. "product", is assigned to the pixels of these images. In addition, images of further components are recorded, which have a different absorption coefficient from the first component. A class value, e.g. "contamination", is also allocated to these pixels. Both data sets are summarized in a table, as represented in FIG. 6, which accordingly contains at least two different class values Y.

According to a further embodiment, for the training only the component 1 can be detected by means of the X-ray detector. Measurement or also simulation data can be stored on the machine for the at least one further component and used to draw up a table as per FIG. 6.

Simulation data of the energy-dependent mass attenuation coefficients (mass attenuation coefficients=absorption coefficient divided by density) of all elements of the periodic table are freely available in databases. From these, the energy-dependent mass attenuation coefficient of molecules, and thus also of material combinations, can be determined.

These data can be held on the machine and used together with real measurement data to determine the mapping rule. For the training, in such cases only the uncontaminated product (component 1) must be detected (scanned) with the X-ray detector, and potential contaminations (i.e. further components) are introduced into the feature table as further rows via simulation data. For this purpose, the mass attenuation coefficient of a potential contamination (typically iron, stainless steel, plastics, glass) is multiplied by an average density of the contamination at the operating temperature as well as by several realistic thicknesses, in order thus to artificially generate the absorption properties of the contaminations. An advantage of this procedure is that a user has to scan only a sufficient number of products (preferably with a cross section of their properties) from their production line for the training process, i.e. has to generate corresponding spectral values by means of the X-ray detector, as the required foreign body data (contamination data) are already available on the machine or are generated via simulation data.

After the training data have been obtained, a mapping rule is sought which—in the case of contrast improvement—transforms the features, on the basis of their class value Y, into another representation form, in particular a so-called score image. The score image has improved properties compared with the raw images. The mapping rule can, however, also carry out a classification directly.

An improved property in this connection is, for example, the spacing of the total image values of a first component (e.g. yogurt) compared with at least one further component (e.g. glass contamination), also called contrast within the framework of this description. The aim is to represent the further (contamination) component in the transformed image more clearly, i.e. with higher contrast, compared with the first component. Ideally, one of the components (usually the first component) is removed, with the result that only all further components are visible.

Which components are to be removed can be controlled via the class value in the table according to FIG. 6, as the mapping rule based on the different class values performs a maximization of the distance between classes. Several different components can be combined to form one class value.

According to a specific variant, for this purpose one mapping coefficient (weighting factor) c is assigned to each energy channel. The thus-formed products are added up, i.e. a linear combination of the features is thus formed.

$$Y_1 = c_1 \cdot \text{channel1}_1 + c_2 \cdot \text{channel2}_1 + \ldots + c_{256} \cdot \text{channel256}_1$$

-continued $$Y_2 = c_1 \cdot \text{channel1}_2 + c_2 \cdot \text{channel2}_2 + \ldots + c_{256} \cdot \text{channel256}_2$$

$$\vdots$$

$$Y_B = c_1 \cdot \text{channel1}_B + c_2 \cdot \text{channel2}_B + \ldots + c_{256} \cdot \text{channel256}_B$$

Methods from the field of multivariate statistics can be used to determine the mapping coefficients c, e.g. a correlation or discriminant analysis.

In the training phase, mapping coefficients c are determined, which are used in the subsequent production phase to calculate the score images (result values). In the production phase, images are recorded and the thus-generated features (i.e. spectral values of the energy channels) are calculated with the mapping coefficients c, whereby new class values Y (result values) are determined, the so-called scores. In the score image, the contrast, thus the spacing of the total image values, between the individual components is significantly increased compared with the raw image. A downstream image processing can distinguish the individual components far more easily (more reliably and with higher sensitivity) in the score image. This is advantageous in particular for a foreign body detection, as false detection is reduced and small or weakly absorbing contaminations are also reliably recognized.

Figure 5:
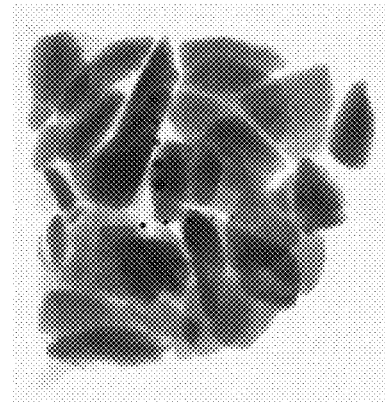
FIG. 5 is a dual energy grayscale image of overlapping products and foreign bodies made of a first and a second material.

FIG. 5 shows a comparison of a grayscale image represented in FIG. 5a, which can be a dual energy image, with two score images, which clearly reveal (FIG. 5b and FIG. 5c) two different types of contamination (made of different materials), which are also faintly recognizable in the grayscale image. In this case, two different mapping rules were thus used in parallel, in order to identify the different types of contamination.

In a further embodiment, the mapping rule is regarded as a classifier, which assigns a class to each pixel in the production phase. The training phase now serves to train the classifier. The table according to FIG. 6 is used for this purpose—analogously to the above-described transformation. For example, a support vector machine (SVM) can be used as classifier. This looks for a hyperplane which optimally separates the two classes, i.e. the first and a further component, which are described by the features (spectral values of the energy channels) from each other. In the simplest case, a hyperplane is a straight line which separates the two groups from each other. If the classes cannot be linearly separated, the features are transferred into a higher-dimensional space, in which they can be linearly separated. This separating line in a higher-dimensional space is referred to as a hyperplane.

In the case of a classifier, the mapping rule is not a transformation of the energy channels into a new image value (score), which has to be further analyzed, as such, but rather directly allocates a class membership (result value) to each pixel (observation).

In a further embodiment, an artificial neural network (ANN) is used. Either this can use the mapping coefficients as prefactors of the spectral values and/or total spectral values—and can thus carry out a transformation like the linear combination outlined above—or the ANN directly represents the classifier which allocates a class value to each pixel (observation) in the production phase.

In a further embodiment, a transformation of the energy channels into a score image is carried out with the aid of factor analysis, in particular also principal component analysis. This performs a transformation of the features (energy channels) on the basis of the variance contained in the data set, without taking into consideration the class values known in the training process.

In addition to the individual spectral values and/or total spectral values of the energy channels which are regarded as features, any desired combinations of the energy channels with each other and/or with themselves are also conceivable. Thus, it can be advantageous that energy channels are, for example, squared and 256 further features are thus generated. A combination of features with each other, so-called mixed terms, is also conceivable. In the above equation, the channels do not occur exclusively linearly, but rather in any desired order. The mapping rule itself is furthermore linear, wherein the input data are pre-processed. This is advantageous in particular when the classes cannot be linearly separated, but a transformation by means of a linear combination is sought, as outlined above.

In the case of the layer thickness determination, the training process is often effected with (at least) two reference materials. Here the layer thickness of a first component varies if the layer thickness of a further component is constant, and then vice versa. For each configuration of reference materials, the layer thicknesses of the two components are known and are used as class value Y in the table according to FIG. 6. In an advantageous embodiment, a separate model is determined for each component contained in the product. For this purpose, a separate table, as represented in FIG. 6, is compiled for each component. A ratio of the first component to the further component can be determined from the ratio of the layer thicknesses. A practical example here is the determination of the fat content in meat, which is often specified as a chemical lean value (CL value).

After the feature table according to FIG. 6 has been created, a mapping rule is in turn sought, which allocates the spectral values and/or total spectral values of the energy channels to a layer thickness of at least one of the components.

In a first embodiment, a linear combination of the spectral values and/or total spectral values (products of energy channels are also possible) is formed, i.e. a mapping coefficient c is allocated to each feature.

$$Y_1 = c_1 \cdot \text{channel1}_1 + c_2 \cdot \text{channel2}_1 + \ldots + c_{256} \cdot \text{channel256}_1$$

$$Y_2 = c_1 \cdot \text{channel1}_2 + c_2 \cdot \text{channel2}_2 + \ldots + c_{256} \cdot \text{channel256}_2$$

$$\vdots$$

$$Y_B = c_1 \cdot \text{channel1}_B + c_2 \cdot \text{channel2}_B + \ldots + c_{256} \cdot \text{channel256}_B$$

In the above equation, Y represents the layer thickness of a component.

The mapping rule for determining layer thicknesses is regarded as a regression problem. In a first embodiment, the mapping coefficients c themselves are determined with the aid of a multiple linear regression (O-PLS, ordinary partial least squares).

In the production phase, the coefficients found are used in order thus to predict a layer thickness Y.

In a further embodiment, an artificial neural network (ANN) is used in order to estimate the layer thickness Y based on the spectral values and/or total spectral values.

Further common methods for solving this regression problem are support vector regression (SVR) or Gaussian process regression (GPR).

In a further embodiment, the (mass) ratio of the components in the product is directly determined instead of the layer thicknesses of the individual components. In the table according to FIG. 6, the class value is now the (mass) ratio of the components and no longer the layer thickness of individual components, from which the (mass) ratio is determined.

As used herein, whether in the above description or the following claims, the terms "comprising," "including," "carrying," "having," "containing," "involving," and the like are to be understood to be open-ended, that is, to mean including but not limited to. Also, it should be understood that the terms "about," "substantially," and like terms used herein when referring to a dimension or characteristic of a component indicate that the described dimension/characteristic is not a strict boundary or parameter and does not exclude variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Any use of ordinal terms such as "first," "second," "third," etc., in the following claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The term "each" may be used in the following claims for convenience in describing characteristics or features of multiple elements, and any such use of the term "each" is in the inclusive sense unless specifically stated otherwise. For example, if a claim defines two or more elements as "each" having a characteristic or feature, the use of the term "each" is not intended to exclude from the claim scope a situation having a third one of the elements which does not have the defined characteristic or feature.

The above described preferred embodiments are intended to illustrate the principles of the invention, but not to limit the scope of the invention. Various other embodiments and modifications to these preferred embodiments may be made by those skilled in the art without departing from the scope of the present invention. For example, in some instances, one or more features disclosed in connection with one embodiment can be used alone or in combination with one or more features of one or more other embodiments. More generally, the various features described herein may be used in any working combination

LIST OF REFERENCE CHARACTERS

100 X-ray inspection device
102 product
104 radiation-generating device
106 X-ray source
108 X-ray detector device
114 spectrally resolving line detector
116 fan-shaped X-ray beam
118 pixel line
122 pixel line
126 carrier
128 housing
130 opening
132 evaluation and control unit
134 data capture unit
136 image processing unit
B movement direction

The invention claimed is:

1. A method for X-ray inspection of products, the method including:
   (a) transmitting X-radiation with a spectral range through a subject product, the subject product being a first product type which is defined as including at least a first component and a second component, the first component having an X-radiation absorption coefficient which is different from an X-radiation absorption coefficient of the second component;
   (b) detecting portions of the X-radiation which have passed through the subject product, the detecting being performed with a spectrally resolving X-radiation detector along a number of adjacent pixels such that the X-radiation detected at each respective pixel is spectrally resolved into a number of energy channels with each respective energy channel assigned a quanta of X-radiation detected at the respective pixel in an energy range defined for the respective energy channel to produce a respective spectral value at each respective energy channel for the respective pixel, the detected portions of X-radiation comprising image data which for each respective pixel includes a respective spectral value for selected or all energy channels of the respective pixel, or a respective total spectral value for each of one or more groups of adjacent energy channels of the respective pixel, or both a respective total spectral value for each of one or more groups of adjacent energy channels of the respective pixel and a respective spectral value for one or more energy channels not included in the one or more groups of adjacent energy channels; and
   (c) assigning a mapping rule to all pixels or to groups of one or more pixels of the number of adjacent pixels, the mapping rule being determined for the first product type and mapping spectral values and total spectral values included in the image data for the respective pixel to a total image value of an image point of a total image for the subject product.

2. The method of claim 1, further comprising determining the mapping rule such that one of: (i) in the total image of a subject product of the first product type, the first component undergoes an enhancement in contrast relative to a reference component, or (ii) the total image value of the image point of the total image of a subject product of the first product type represents a value for a total thickness of the first component or the second component, viewed in the direction in which the X-radiation is transmitted.

3. The method of claim 1, wherein the mapping rule represents a classifier which assigns one of the first component and the second component to a predefined class.

4. The method of claim 3, wherein the classifier comprises an artificial neural network or a support vector machine.

5. The method of claim 1, further comprising: determining the mapping rule such that a respective mapping coefficient is assigned to each spectral value and each total spectral value included in the image data for a respective pixel; and generating the total image of the subject product includes multiplying each spectral value and each total spectral value by the mapping coefficient assigned to the respective spectral value and total spectral to produce a respective product for the respective spectral value and total spectral value and adding the products produced for the respective spectral value and the respective total spectral value together.

6. The method of claim 5, wherein the mapping rule assigns a first mapping coefficient to each spectral value and each total spectral value included in the image data for a first group of adjacent energy channels for a respective pixel and assigns a second mapping coefficient to each spectral value and each total spectral value included in the image data for a second group of adjacent energy channels different from the first group of adjacent energy channels such that the total image for the subject product comprises a multiple energy image.

7. The method of claim 6, wherein the first group of adjacent energy channels do not overlap spectrally with the second group of adjacent energy channels.

8. The method of claim 1, wherein:
(a) the mapping rule for the first product type is determined by a machine learning process in which, in a learning mode, a number of training products which each include one of the first component and the second component, and not both the first component and the second component, and which each have a different thickness are subjected to the X-radiation and the X-radiation passing therethrough is detected by the spectrally resolving X-radiation detector;
(b) for selected pixels or for groups of adjacent pixels of the number of adjacent pixels, each spectral value or total spectral value which is detected for a respective training product represents a respective feature of the mapping rule; and
(c) a respective class value is assigned as a target value of the mapping rule, wherein the respective class value corresponds to a respective component detected in the learning mode.

9. The method of claim 8, wherein a linear combination of the respective features comprises a representation of the mapping rule, and wherein a respective mapping coefficient for each feature of the respective features is determined with a correlation analysis or a discriminant analysis.

10. The method of claim 1, further comprising determining the mapping rule for the first product type by simulation data generated for the first product type using known values for an energy-dependent absorption coefficient for the X-radiation and known thickness.

11. The method of claim 1, wherein:
(a) the mapping rule and a second mapping rule are determined by a machine learning process, the mapping rule for determining a total thickness of the first component, and the second mapping rule for determining a total thickness of the second component;
(b) in a learning mode, a number of training products which include both the first component and the second component are subjected to the X-radiation and the X-radiation passing therethrough is detected by the spectrally resolving X-radiation detector, and one of:
(i) training products which have in each case a different previously known total thickness of the first component and an identical total thickness or different total thickness of the second component are used to determine the mapping rule, and training products which have in each case a different previously known total thickness of the second component and an identical total thickness or different total thickness of the first component are used to determine the second mapping rule, or
(ii) training products which have in each case a different previously known total thickness of the first component and an identical total thickness or a different previously known total thickness of the second component are used to determine the mapping rule and second mapping rule; and
(c) for selected pixels or for groups of adjacent pixels of the number of adjacent pixels, the spectral values or total spectral values which are detected for the training products represent features of the mapping rule and the second mapping rule, and in each case a respective previously known total thickness is assigned as a target value of the mapping rule and the second mapping rule.

12. The method of claim 11, wherein the mapping rule represents a regression problem formed by a multiple regression or an artificial neural network.

13. The method of claim 1:
(a) wherein additional product types are defined, each respective additional product type comprising products which include in each case the first component and at least one respective additional component, each respective additional component having an X-radiation absorption coefficient different from the X-radiation absorption coefficient of the first component;
(b) further including generating at least one additional total image of the subject product from the image data of the subject product; and
(c) wherein, for a respective one of the additional product types, a respective additional mapping rule is used to generate a respective additional total image.

14. A device for X-ray inspection of products, the device including:
(a) a radiation-generating device including at least one X-ray source for generating X-radiation with a spectral range;
(b) a spectrally resolving X-radiation detector operable for detecting the X-radiation that has passed through a subject product at each of a number of adjacent pixels of the spectrally resolving X-radiation detector such that the X-radiation detected at each respective pixel is spectrally resolved into a number of energy channels with each respective energy channel assigned a quanta of X-radiation detected at the respective pixel in an energy range defined for the respective energy channel to produce a respective spectral value at each respective energy channel defined for the respective pixel, the detected X-radiation comprising image data which for each respective pixel includes a respective spectral value for selected or all energy channels of the respective pixel, or a respective total spectral value for each of one or more groups of adjacent energy channels of the respective pixel, or both a respective total spectral value for each of one or more groups of adjacent energy channels of the respective pixel and a respective spectral value for one or more energy channels not included in the one or more groups of adjacent energy channels; and
(c) an evaluation and control unit operatively connected to receive the image data and for assigning a mapping rule to all pixels or to groups of one or more pixels of the number of adjacent pixels, the mapping rule being determined for a first product type and mapping spectral values and total spectral values included in the image data for the respective pixel to a total image value of an image point of a total image for the subject product.

15. The device of claim 14, wherein the evaluation and control unit is additionally operable in a learning mode in which,
  (a) a number of training products which each include one of a first component and a second component of the first product type and which each have a respective different thickness are subjected to the X-radiation and the X-radiation passing therethrough is detected by the spectrally resolving X-radiation detector;
  (b) for selected pixels or for groups of adjacent pixels of the number of adjacent pixels, each spectral value or total spectral value which is detected for a respective training product represents a respective feature of the mapping rule; and
  (c) a respective class value is assigned as a target value of the mapping rule, wherein the respective class value corresponds to a respective component detected in the respective training product.

16. The device of claim 14, wherein the evaluation and control unit has a memory in which the mapping rule for the first product type is stored together with, for each additional product type of one or more additional product types, a respective additional mapping rule.

* * * * *